(12) United States Patent
Rahman et al.

(10) Patent No.: US 8,287,921 B1
(45) Date of Patent: Oct. 16, 2012

(54) FORMULATIONS AGAINST CUTANEOUS LEISHMANIASIS

(76) Inventors: Attaur Rahman, Karachi (PK); Mohammad Iqbal Choudhary, Karachi (PK); Sammer Yousuf, Karachi (PK); Samreen Khan, Karachi (PK); Farooq Rahman Soomro, Karachi (PK); Shahida Perveen, Karachi (PK)

( * ) Notice: Subject to any disclaimer, the term of this patent is extended or adjusted under 35 U.S.C. 154(b) by 0 days.

(21) Appl. No.: 13/189,509

(22) Filed: Jul. 24, 2011

(51) Int. Cl.
  *A01N 65/00* (2009.01)

(52) U.S. Cl. .................................................... 424/725
(58) Field of Classification Search ................ None
  See application file for complete search history.

(56) References Cited

U.S. PATENT DOCUMENTS

2003/0175366 A1* 9/2003 Pauly et al. .................. 424/725

* cited by examiner

*Primary Examiner* — Michael Meller
(74) *Attorney, Agent, or Firm* — Sarfaraz K. Niazi

(57) ABSTRACT

Treatment of leishmaniasis in animals and humans using the methanolic extract of *Physalis minima* in petrolatum is described.

1 Claim, No Drawings

FORMULATIONS AGAINST CUTANEOUS LEISHMANIASIS

Physalins are the steroidal lactone constituents of *Physalis* and other closely related genera, belonging to the family Solanaceae. The *P. minima* (Linn-Var. Indica) is a herb widely used in folk medicines. The plants of the genus *Physalis* possess a number of interesting biological properties including anti-inflammatory, immunomodulatory and antiparasitic. (1, 2)

Leishmaniasis is caused by protozoa parasites of the genus *Leishmania*, a biologically diverse group of flagellate parasites of the Trypanosomatidae family, which can be differentiated by genetic, biochemical, and immunological studies. Leishmaniasis typically occurs in the Old World around the Mediterranean Sea, in East and West Africa, Afghanistan, Pakistan, India, Nepal, Bangladesh, and in China. In the New World, this disease is found in the southern parts of the United States to the northern pats of Argentina and Paraguay. Both domestic and wild animals are main reservoirs of *Leishmania* parasites, while the female flying insects of the genera *Phlebotomus* and *Lutzomya* are the vectors of Leishmaniasis. The secondary metabolites of plants, alkaloids, quinines, and terpenes, have been used to cure protozoan parasitic diseases. The use of quinine and emetine are best examples for the treatment of parasitic diseases such as malaria and amoebiasis. (3)

Some natural products have also shown leishmanicidal activities. Diospyrin, isolated from *Diospyros mantana*, is active against *L. donovani* (4); berberine is effective against cutaneous Leishmaniasis in rats; and harmaline, which was isolated from *Peganum harmala*, shows antiprotozoal action.

Optimal activity of natural products is unpredictable and the effectiveness of the whole extract of *Physalis minima* has not been optimized. The instant invention reports the surprising activity of the methanolic extract of *Physalis minima* against leishmania parasite.

In this invention, organic and aqueous extracts of *Physalis minima* were tested as potential treatment of leishmaniasis, more particularly cutaneous infections. As an example, methanol extract was prepared first by crushing a 20 Kg sample of air dried aerial part of plant and soaking it in 100 L methanol for 4 to 5 days, by this 2.0 kg methanolic extract was obtained. Methanol was removed by rotary evaporator under vacuum; the extract was further also air-dried in room temperature to prepare a solvent-free final solid extract. The methanolic extract was made such that a 2.0 kg of solid weight of component was obtained from 20 kg of wet aerial part of the plant. The same method was used for other solvent systems such as petroleum ether, ethyl acetate, methanol:water (1:1) mixture and chloroform.

The solvent extracts listed above were tested for their leishmanicidal assay, cytotoxic activity, and toxicity. An ointment formulation of the extracts was prepared and tested in animal models and humans; it was discovered that the optimal results are obtained when the methanolic extract is formulation in a topical ointment comprising the extract the petrolatum.

In Vitro Leishmanicidal Assay

*Leishmania* promastigotes were grown in bulk early in modified NNN biphasic medium using normal physiological saline. *Leishmania* parasite promastigotes were cultured with RPMI 1640 medium (Sigma, St. Louis, USA) supplemented with 10% heat inactivated foetal Calf serum (FCS) (PAA Laboratories GmbH, Austria) Parasites at log phase were centrifuged at 2000 rpm for 10 minutes, and washed three times with saline at same speed and time. Parasites were diluted with fresh culture medium to a final density of $1\times10^6$ cells/ml.

In a 96-well micro titer plate, medium was added in different wells, 20 μl of the experimental compound was added in medium and serially diluted. 100 μl of parasite culture was added in all wells. Two rows were left for negative and positive control. Negative controls receives medium while the positive control contains varying concentrations of standard antileishmanial compound e.g., Amphotericin B (MP Biomedical Inc.), Pantamidine (ICN Biomedical Inc.). The plate was incubated between 22-25° C. for 72 hrs. The culture was examined microscopically on an improved Neubaure counting chamber and Software Ezfit 5.03 Perella Scientific calculated IC50 values of fractions possessing antileishmanial activity. All assays were run in duplicate (5). Table 1 reports the leishmanicidal activities of the extracts studied. While all extracts showed significant activity, it was highest for the chloroform extract and the lowest for the ethyl acetate extract when compared to standards drugs.

TABLE 1

In vitro Leishmanicidal activity:

| Medicinal Plant | Plant's Extracts | ($IC_{50}$ μg/mL ± S.D) |
|---|---|---|
| *Physalis minima* Linn. | Petroleum ether | 13.62 ± 0.30 |
| (Sun berry) | Chloroform | 2.05 ± 0.02 |
| | Methyl alcohol | 26.00 ± 0.59 |
| | Ethyl acetate | 35.36 ± 0.08 |
| | Methanol:Water (1:1) | 5.70 ± 0.07 |
| Amphotericin B, standard | n/a | 0.12 ± 0.10 |
| Pentamidine, standard | n/a | 5.13 ± 0.02 |

Cytotoxic Activity Against 3T3 Cell Lines:

Cytotoxic activity of compounds was evaluated in 96-well flat-bottomed micro plates by using the standard MTT (3-[4,5-dimethylthiazole-2-yl]-2,5-diphenyl-tetrazolium bromide) colorimetric assay1. For this purpose, 3T3 (Mouse fibroblast) were cultured in Dulbecco's Modified Eagle's Medium, supplemented with 5% of foetal bovine serum (FBS), 100 IU/mL of penicillin and 100 μg/mL of streptomycin in 25 $cm^3$ flask, and kept in 5% CO2 incubator at 37° C. Exponentially growing cells were harvested, counted with haemocytometer and diluted with a particular medium. Cell culture with the concentration of $1\times10^5$ cells/mL was prepared and introduced (100 μL/well) into 96-well plates. After overnight incubation, medium was removed and 200 μL of fresh medium was added with different concentrations of compounds (1-100 μg/mL). After 72 h, 50 μL MTT (2 mg/mL) was added to each well and incubated further for 4 hrs. Subsequently, 100 μL of DMSO was added to each well. The extent of MTT reduction to formazan within cells was calculated by measuring the absorbance at 570 nm, using a microplate ELISA reader (Spectra Max plus, Molecular Devices, CA, USA). The cytotoxicity was recorded as concentration causing 50% growth inhibition for 3T3 cells. We also observed that some extracts showed anticancer activity for the prostate cancer cell line PC3 (6).

TABLE 2

In vitro cytotoxic activity against 3T3
cell lines (Normal Fibroblast cell)

| Extracts | $IC_{50}$ (μg/mL) ± S.D. 3T3 cell lines | Standard (Cyclohexamide) |
|---|---|---|
| Petroleum ether | >100 | 0.26 ± 0.04 |
| Methanol | 18.78 ± 0.21 | |
| Chloroform | 13.31 ± 0.70 | |
| Ethyl acetate | >100 | |
| Methanol:water (1:1) | >100 | |

Toxicity Determination ($LD_{50}$)

Toxicity was determined of soluble fraction of *Physalis minima* in term of $LD_{50}$. Animals were given doses orally ranges from 100 mg to 1200 mg/Kg and observed that 48 hrs. Lethality was not observed up to dose of 1200 mg/Kg.

TABLE 3

Animal Toxicity Determination.

| Animal model | Doses (mg/Kg) | $LD_{50}$ or Lethality |
|---|---|---|
| Wister Rats (Male 200-250 g) | 10 | No Lethality |
| | 100 | No Lethality |
| | 500 | No Lethality |
| | 1000 | No Lethality |

Topical Ointment Preparation

Chemotherapeutic agents with potential or established antileishmanial activity have been incorporated in different ointment and cream formulations and tested for their efficacy when applied topically. For the preparation of ointment we used methnolic extracts of *Physalis minima* in white soft paraffin of pharmaceutical grade. The final concentration of extract was 0.25 g per gram of final ointment. This means 25% (w/w) methanolic extract of *Physalis minima* with white soft paraffin-based petroleum gel. Other concentrations of extract tested included: 5%, 10%, and 20%; the 25% methanolic extract of *Physalis minima* with white soft paraffin-based petroleum gel gives optimal results.

In Vivo Assay on BALB/c Mice

The mice were inoculated in the base of the tail with $1 \times 10^6$ to $5 \times 10^6$ infective promastigotes. The development of the lesion was followed macroscopically, and the presence of parasites in biopsy material was monitored microscopically in both smears and cultures. Material aspirated with a fine glass pipette through a small incision made at the margin of the lesion with a sterile surgical blade and stained with Giemsa and cultured as previous described. Then topically apply the prepared ointment to the lesions twice a day for 4 weeks. Measure the lesions size by vernier caliper at every 4-5 days of treatment. The lesions completely cure within 12 weeks (7).

Human Clinical Trials

Human clinical trials have been done on 100 patients for *Physalis minima* extracts with soft paraffin ointment. Out of 100 subjects, 35 patients come for two weeks follow up. Out of 35, 23 patients (65.71%) showed excellent response and come to recovery by the topical application.

CONCLUSION

In short it can be concluded that this new invention as ointment preparation containing active ingredient in plants extracts is capable of eliminating the parasites and healing the wound because of its anti-Leishmanial activity when applied directly to the lesion. This preparation is non-invasive material easy to comply and apply. It has good absorption with no notable local/systemic effects.

REFERENCES

1. M. Iqbal Choudhary, Sammer Yousaf, Shakil Ahmed, Samreen, Kausar Yasmeen, and Atta-ur-Rahman, "Antileishmanial Physalins from *Physalis minima*", *Chem & Biodiv.*, Vol. 2 (2005).
2. M. Iqbal Choudhary, Sammer Yousaf, Samreen, Shakil Ahmed, and Atta-ur-Rahman, "New leishmanicidal physalins from *Physalis minima*", *Nat. Prod. Res.*, Vol. 21, No. 10, August 2007, 877-883.
3. M. J. Chan-Bacab, L. M. Pefia-Rodriguez, *Nat. Prod. Rep.* 2001, 18, 674.
4. B. Hazra, A. K. Saha, R. Ray, D. K. Roy, P. Sur, A. Banerjee, *Trans. R. Soc. Trop. Med. Hyg.* 1987, 81, 738.
5. Solomon Habtemariam. "In vitro antileishmanial effects of antibacterial diterpenes from two Ethiopian Premna species: *P. schimperi* and *P. oligotricha*" *BMC Pharmacology*, 2003, 3:6.
6. Mosmann, T. *J. Immunol. Methods* 1983, 65, 55-63
7. M. Iqbal Choudhary, Sammer Yousaf, Samreen, Shakil Ahmed, and Atta-ur-Rahman, "New leishmanicidal physalins from *Physalis minima*", *Nat. Prod. Res., Vol.* 21, No. 10, August 2007, 877-883.

We claim:

1. A composition for treating leishmaniasis in warm blooded animals and humans consisting essentially of a therapeutically effective amount of an ethyl acetate extract of aerial parts of *Physalis minima* dispersed in petroleum.

* * * * *